United States Patent [19]

Berg et al.

[11] Patent Number: 5,224,475
[45] Date of Patent: Jul. 6, 1993

[54] METHOD AND APPARATUS FOR TERMINATION OF VENTRICULAR TACHYCARDIA AND VENTRICULAR FIBRILLATION

[75] Inventors: Gary L. Berg, Edina; Martin A. Rossing, Ramsey; David K. Peterson, Mounds View; Robert A. Neumann, Blaine, all of Minn.

[73] Assignee: Medtronic, Inc., Minneapolis, Minn.

[21] Appl. No.: 795,211

[22] Filed: Nov. 20, 1991

[51] Int. Cl.⁵ .............................................. A61N 1/39
[52] U.S. Cl. .................................. 128/419 D; 128/734
[58] Field of Search ............ 128/419 D, 419 PT, 734, 128/908

[56] References Cited

U.S. PATENT DOCUMENTS

| | | | |
|---|---|---|---|
| 4,140,131 | 2/1979 | Dutcher et al. | 128/419 PT |
| 4,164,215 | 8/1979 | Finlayson et al. | 128/419 D |
| 4,164,946 | 8/1979 | Langer | 128/419 D |
| 4,771,781 | 9/1988 | Lerman | 128/419 D |
| 4,870,341 | 9/1989 | Pihl et al. | 128/419 D |
| 4,899,750 | 2/1990 | Ekwall | 128/419 PG |
| 5,003,975 | 4/1991 | Hafelfinger et al. | 128/419 PG |
| 5,097,830 | 3/1992 | Eikefjord et al. | 128/419 D |
| 5,107,834 | 4/1992 | Ideker et al. | 128/419 D |

Primary Examiner—Kyle L. Howell
Assistant Examiner—Kennedy J. Schaetzle
Attorney, Agent, or Firm—Reed A. Duthler; Harold R. Patton

[57] ABSTRACT

An implantable defibrillator provided with a plurality of defibrillation electrodes, which may be reconfigured to define a plurality of defibrillation pathways. The device is capable of measuring the impedance along a selected defibrillation pathway, during delivery of an impedance pulse, and monitoring the success or failure of the pulse to accomplish defibrillation or cardioversion. In response to a detected failure to accomplish cardioversion in conjunction with a measured change of impedance of greater than a predetermined amount, a new defibrillation pathway is selected, which may employ some or all of the electrodes employed to define the original impedance pathway. The device also includes apparatus for varying the relative amplitude of defibrillation pulses applied to individual electrodes used in sequential or simultaneous, multiple electrode pulse regimens, in order to equalize current distribution, in response to measured pathway impedances.

10 Claims, 8 Drawing Sheets

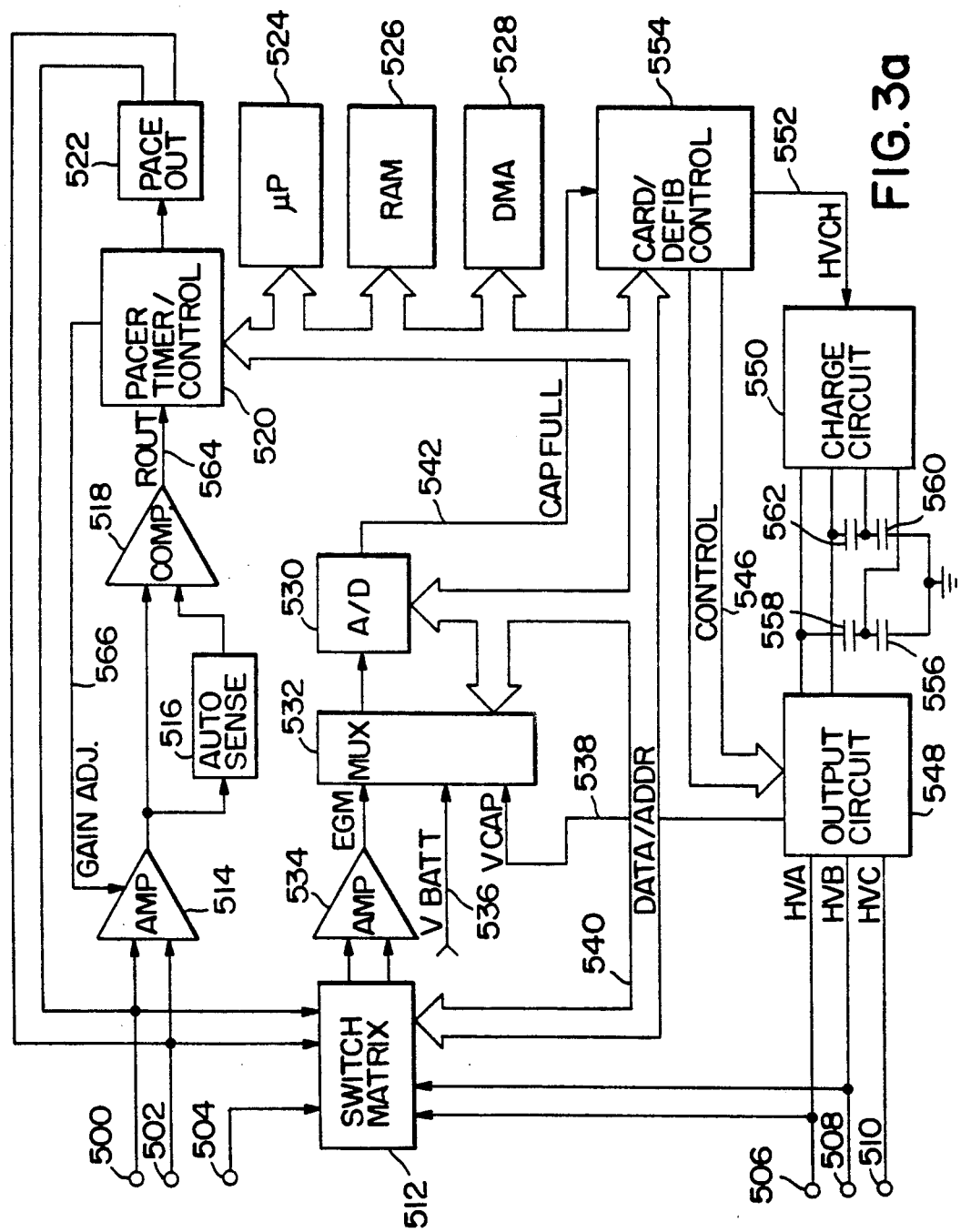

| THERAPY MENU | | | |
|---|---|---|---|
| NO. | THERAPY TYPE | PATHWAYS | AVAIL? |
| 1 | SIMULTANEOUS | HVA+HVB → HVC | NO |
| 2 | SIMULTANEOUS | HVA+HVC → HVB | YES |
| 3 | SINGLE PAIR | HVA → HVC | YES |
| 4 | SINGLE PAIR | HVB → HVC | YES |

FIG. 5a

| THERAPY MENU | | | |
|---|---|---|---|
| NO. | THERAPY TYPE | PATHWAYS | AVAIL? |
| 1 | SEQUENTIAL | HVA → HVC, HVB → HVC | NO |
| 2 | SEQUENTIAL | HVA → HVB, HVC → HVB | YES |
| 3 | SINGLE PAIR | HVA → HVC | YES |
| 4 | SINGLE PAIR | HVB → HVC | YES |

FIG. 5b

| IMPEDANCE HISTORY | | | |
|---|---|---|---|
| PATHWAY | STATUS | Ω | TIME |
| HVA + HVB → HVC | BAD | 50<br>60<br>15 | 12:25:7:30<br>1:09:3:15<br>4:13:16:08 |
| HVA + HVC → HVB | GOOD | 75 | 4:13:16:08 |
| HVC + HVB → HVA | GOOD | | |
| | | | |

FIG. 6a

| IMPEDANCE HISTORY | | | |
|---|---|---|---|
| PATHWAY | STATUS | Ω | TIME |
| HVA − HVC | BAD | 75<br>90<br>140 | 5:11:6:14<br>8:12:15:09<br>9:02:7:29 |
| HVB − HVC | GOOD | 62<br>51<br>38 | 8:12:15:09<br>9:02:7:29<br>9:02:7:29 |
| HVA − HVB | GOOD | 56 | 9:02:7:29 |

FIG. 6b

METHOD AND APPARATUS FOR TERMINATION OF VENTRICULAR TACHYCARDIA AND VENTRICULAR FIBRILLATION

BACKGROUND OF THE INVENTION

This invention relates to implantable stimulators generally and more particularly to implantable cardioverters and defibrillators.

Over the past 20 years, there has been substantial work toward developing a practical, implantable defibrillator. However, several significant problems still remain. Early conceptions of implantable defibrillators, such as disclosed in U.S. Pat. No. RE 27,652 by Mirowski et al., envision a system employing a ventricular endocardial electrode and a plate electrode, mounted directly to the heart, subcutaneously, or applied to the skin. However, it was recognized early on that a totally transvenous system would be desirable in order to simplify the use of implantable defibrillators. One such system is suggested in U.S. Pat. No. 3,942,536 by Mirowski et al., which discloses a transvenous lead having electrodes intended for location in the right ventricular apex and superior vena cava. Such systems were eventually tested in human beings with some success. However, currently available commercial versions of implantable defibrillators generally employ epicardial patch electrodes alone or in conjunction with transvenous electrodes.

While systems employing epicardial patch electrodes are workable, a thoracotomy is required in order to apply the epicardial electrode or electrodes. It is generally believed that it would be highly desirable to produce an implantable defibrillator which would entirely avoid the necessity of a thoracotomy, and there has been substantial work directed toward such systems, as disclosed in U.S. Pat. No. 4,727,877 issued to Kallok and U.S. Pat. No. 4,708,145 issued to Tacker et al. Both Tacker et al. and the Kallok patents disclose the use of a transvenous, two-electrode lead in combination with a subcutaneous patch electrode.

U.S. Pat. No. 4,392,407 issued to Williams et al. and co-pending. commonly assigned applications 284,957 by Mehra and 284,955 by Bardy, both filed Dec. 15, 1988 disclose multiple electrode systems employing subcutaneous patch electrodes, coronary sinus/great vein electrodes, and ventricular endocardial electrodes. These electrode systems and other multiple electrode systems employing endocardial electrodes alone or in conjunction with subcutaneous electrodes appear to hold significant promise.

Where there are electrical conductors there is the possibility of electrical malfunction. In the context of pacing leads, these malfunctions have often taken the form of open circuits or short circuits, and monitoring systems have been developed to detect and remedy these problems. U.S. Pat. No. 4,140,131 issued to Dutcher, incorporated herein by reference in its entirety, discloses a pacemaker which ascertains the presence of short circuits or open circuits by measuring the impedance between the pacing electrodes and determining whether the measured impedance falls outside a predetermined range. If the measured impedance falls outside this range, a warning signal is communicated to the patient in whom the pacer is implanted by means of electrical stimulation of the tissue adjacent the pacer. A more recent example of a pacemaker which measures impedance is disclosed in U.S. Pat. No. 4,899,750 issued to Ekwall, and incorporated herein by reference in its entirety. In this pacer, measurements of impedance are stored in a log for later review by the physician to allow diagnosis of lead related problems. In some pacemakers, lead configuration is programmable between unipolar and bipolar configurations. This feature raises the possibility that the pacer may be programmed to a configuration incompatible with the leads actually implanted. The pacer disclosed in published EPO Patent Application No. 338,363, also incorporated herein by reference in its entirety, addresses the problem of inappropriate lead configuration programming by measuring impedance between pacing electrodes whenever reprogramming has taken place and reconfigures the programming of the lead configuration if the measured impedance indicates that the expected lead system is not present. The pacer also measures impedance in response to a failure to capture or other circumstances indicative of lead malfunction and reprograms the lead configuration in response to a measured impedance indicative of an electrical fault. Lead configurations are programmed and tested until a configuration exhibiting appropriate values of measured impedance is selected.

SUMMARY OF THE INVENTION

The present invention provides a mechanism for optimizing electrode configuration in the context of an implantable cardioverter/defibrillator provided with a plurality of defibrillation electrodes and the ability to deliver pulses between differing combinations of individual ones of the electrodes, or all of the electrodes together. For example, the invention may usefully be practiced in the context of an implantable cardioverter/defibrillator provided with right ventricular, coronary sinus and subcutaneous electrodes. Electrode systems consisting entirely of epicardial electrodes and electrode systems employing other transvenously inserted electrodes such as superior vena cava electrodes may also be used beneficially in conjunction with the present invention.

The cardioverter/defibrillator is provided with an internal therapy menu, listing particular electrode configurations in a predetermined order. Each therapy regimen listed will specify the pathways for pulse delivery employed during that particular regimen. For example, in a system employing right ventricular, coronary sinus and subcutaneous electrodes, a sequential pulse regimen may be selected in which pulses are delivered sequentially along a first pathway between the right ventricular electrode and the coronary sinus electrode and along a second pathway between the right ventricular electrode and the subcutaneous electrode. During delivery of the pulses, impedance for each pathway is measured, and is compared to the previously recorded measured impedance for that pathway. Following delivery of the pulses, the underlying cardiac rhythm is assessed to determine whether the pulses were successful in terminating the cardiac arrhythmia that led to the delivery of the cardioversion or defibrillation pulses. In the event that the impedance along at least one of the pathways involved in the pulse regimen delivered differs more than a predetermined amount from the previously measured impedance along the same pathway or from a predefined impedance baseline, and the pulse regimen was unsuccessful in terminating the arrhythmia, the pulse pathway is marked as "bad" in an internal impedance history log within the cardioverter/defibrillator.

Following the marking of a delivery pathway as "bad", the device scans the therapy menu to find the next available therapy, checking to determine whether it employs pathways marked as "bad". When it locates a therapy regimen which has no pathways marked as "bad", it schedules this pulse regimen or therapy for delivery following the next detection of an arrhythmia, or following a redetection of arrhythmia following the delivery of the preceding cardioversion or defibrillation pulses. In more advanced embodiments, it is anticipated that the device may automatically inventory the available electrodes and generate its own alternative therapy regimens if the physician's specified therapy menu is exhausted.

In practical implementations of the invention, it is anticipated that the physician will prefer that the pulse amplitude associated with the next available therapy will be determined using the same criteria that would apply to control delivery of successive attempts using the original electrode configuration and pulse regimen. Generally, therefore, the pulse amplitude will increase with each successive attempt, even when the electrode configuration has been altered. However, in some cases, physicians may wish to begin using a new electrode configuration and/or pulse regime at the same pulse amplitude as used with the previous unsuccessful attempt using the original electrode configuration or the pulse amplitude specified for the initial attempt to cardiovert or defibrillate. Therefore, it is anticipated that this aspect of the device's functioning will be made subject to external programmer control.

The present invention, unlike systems directed toward detection of shorts and open circuits in pacing leads does not require that the next therapy selected necessarily cease to employ any of the defibrillation electrodes associated with the pathway marked "bad". For example, let it be assumed that the initially selected therapy comprises a simultaneous pulse, multiple electrode regimen in which the coronary sinus and subcutaneous plate electrodes are tied together and a pulse is delivered between these two electrodes and the right ventricular electrode. Upon detection that this pathway (CS+SQ−RV) is bad, the device may then move on to try the next scheduled therapy, for example a simultaneous pulse multiple electrode regimen in which the right ventricular and coronary sinus leads are tied together, and a pulse is delivered between these two electrodes and the subcutaneous plate electrode (RV+CS−SQ).

Alternatively, let it be assumed that the initial therapy selected is a sequential pulse regimen in which pulses are delivered first between the coronary sinus electrode and the right ventricular electrode and subsequently between the right ventricular electrode and the subcutaneous electrode, and that the pathway between the coronary sinus electrode and right ventricular electrode (RV −CS) is marked as bad. The next subsequent therapy may be a multiple pulse regimen in which pulses are delivered sequentially between the coronary sinus and subcutaneous electrodes (CS−SQ) and between the right ventricular and subcutaneous electrodes (RV−SQ), and not employing the CS−RV pathway.

Unlike the reconfiguration of pacing systems as described in the above-cited references, the present invention is also capable of responding to changes in the pulse delivery pathways other than short circuits and open circuits within individual leads. For example, in either of the two examples set forth above, the change in impedance might be due to migration or poor initial location of either the right ventricular electrode or the coronary sinus electrode such that the electrodes are in excessively close proximity to one another at some point. This problem, while it may preclude the use of the RV−CS pathway, does not necessarily preclude usage of the electrodes in other pulse delivery regimens which do not use this pathway. Similarly, even if two or more electrodes are located on the same defibrillation lead, a short circuit or a failure in the insulation separating the conductors coupled to the two electrodes need not entirely preclude their use in delivery of subsequent therapies, so long as the therapies delivered do not employ the pathway between the two electrodes. Similar problems associated with epicardial lead systems may also be addressed.

The present invention is particularly optimized for use in conjunction with an implantable cardioverter/defibrillator. It is substantially more important in cardioverters and defibrillators than in pacemakers that each individual defibrillation pulse or pulse regimen delivered be effective. Sequential unsuccessful defibrillation attempts are painful, and in the worst case may result in failure to terminate fibrillation, leading to serious injury or death. For this reason, even in the case where a significant change in impedance is noted which would trigger a change in electrode configuration if the delivered therapy is ineffective, the electrode configuration will remain unaltered if the therapy proves to be effective. In this fashion, a known electrode configuration which has proven to be effective is not prematurely discarded. Further, if preimplant testing of the patient indicates, for example, that the patient is generally more easily cardioverted or defibrillated using multiple electrode configurations, the present invention makes it possible to check for other available multiple electrode configurations prior to abandoning one of the electrodes and reverting to a single pair of electrodes, which may require higher amplitude pulses in order to successfully terminate detected arrhythmias.

The invention also assists in accomplishing cardioversion or defibrillation with the least possible energy expenditure. By reducing the number of shocks given, less energy is used per cardioversion or defibrillation attempt. By selecting shock pathways which are determined to be usable, the unnecessary repetition of unsuccessful pulse regimens is avoided. Reducing the number of unsuccessful defibrillation or cardioversion pulses should also result in a shortening of the average duration of cardioversion and defibrillation attempts. This should benefit the patient by reducing the time during which the heart is ischemic and should thus reduce the potential damage to heart tissue due to lack of blood supply.

The present invention may also be employed in conjunction with an impedance sensing system specifically directed to detection of open circuits or dead shorts, as in the prior art. In this case, open circuit or short detection should require a change in measured impedance substantially greater than the increase in impedance necessary to trigger a change in the selected pulse regimen. For example, a moderate but significant change in impedance, e.g., 50%, in conjunction with failure to defibrillate may trigger a change in electrode configuration, while a substantially greater change in impedance may be used to detect an actual open circuit or fractured lead conductor. Alternatively, measured impedances outside of a predetermined range may be used as indicative of a short or open circuit. Detection of a short or open circuit, may result in the pathway so measured being abandoned, regardless of the efficacy of the delivered therapy.

The present invention measures the impedance during delivery of high voltage cardioversion or defibrillation pulses to detect overall changes in the performance of the defibrillation pathway between the electrodes, rather than simply detecting a mechanical or electrical failure of the electrodes and associated leads. This aspect of the invention is directed toward optimization of the electrode configuration and pulse regimen then mere operability and should be kept in mind when reading the more detailed disclosure of the invention, below.

The impedance measurement of the present invention may also be employed to adjust the relative amplitude of the defibrillation pulses delivered along the individual shock pathways. For example, in the context of a therapy regimen employing multiple pathways, it is determined that one pathway has an acceptable, but significantly higher impedance than the other pathway, a higher voltage pulse may be delivered across the high impedance pathway. This should result in a reduced pulse width for a given pulse energy, and a relatively increased current density during the pulse. This aspect of the invention is best practiced in a device which employs multiple, independently chargeable capacitor banks so that the capacitor banks coupled to individual shock pathways may be charged to different amplitudes in order to accomplish a more uniform current density throughout the heart during delivery of the defibrillation pulse. This approach is believed to provide substantial advantages due to the ability to reduce the overall energy expenditure required to achieve a current density across the heart that is sufficient to cause depolarization of a sufficient percentage of heart tissue to terminate the tachycardia of fibrillation episode in progress.

BRIEF DESCRIPTION OF THE DRAWINGS

The above and still further objects, features and advantages of the present invention will become apparent from the following detailed description of a presently preferred embodiment, taken in conjunction with the accompanying drawings, and, in which:

FIGS. 3a and 3b are schematic block diagrams illustrating the structure of two embodiments of an implantable pacemaker/cardioverter/defibrillator in which the present invention may be practiced.

FIGS. 5a and 5b are examples of therapy menus illustrative of the operation of the present invention.

FIGS. 6a and 6b are examples of impedance history records illustrative of the operation of the present invention.

DETAILED DESCRIPTION OF THE PREFERRED EMBODIMENT

Figure 1:
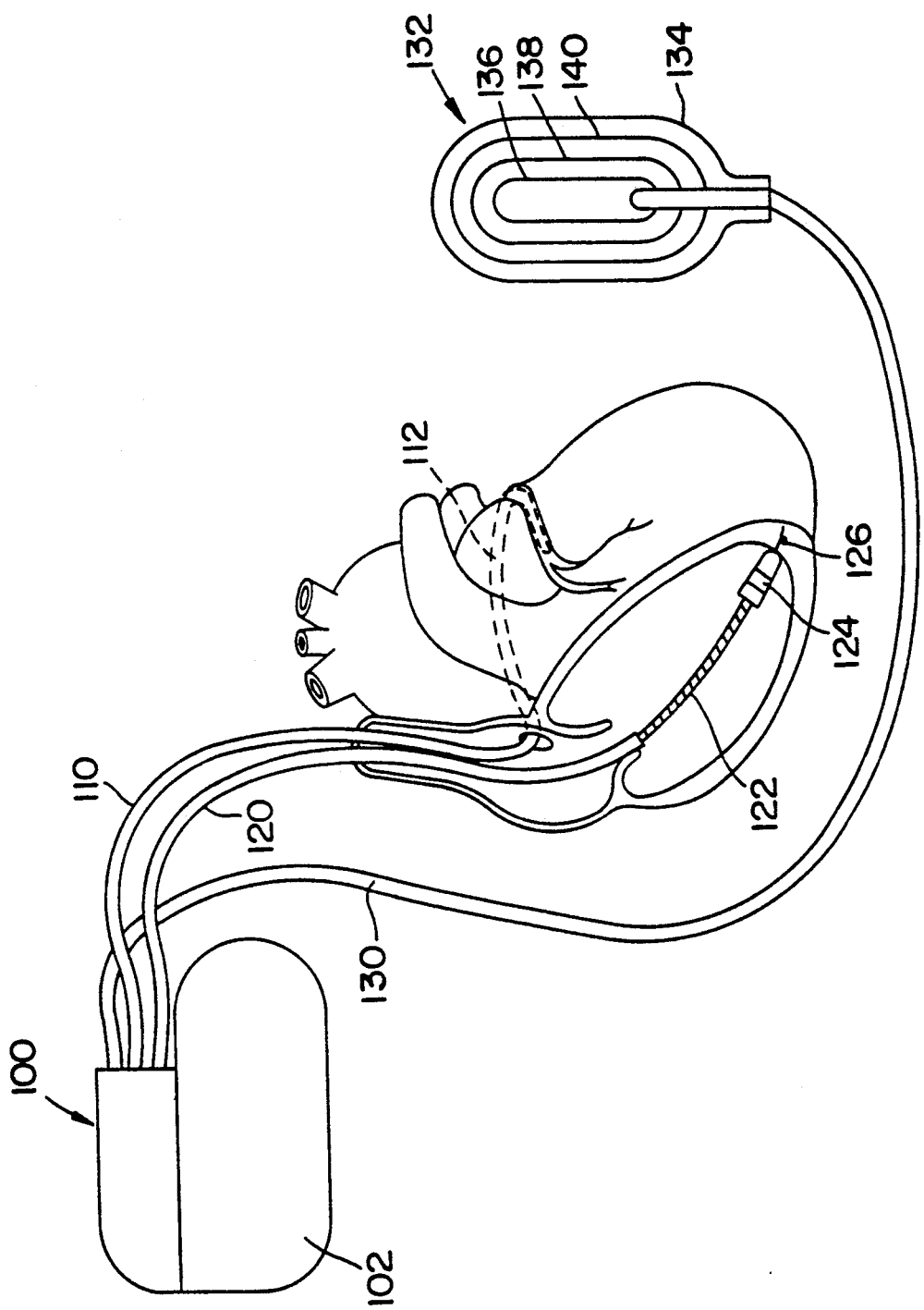
FIG. 1 is an illustration of an implantable pacemaker/cardioverter/defibrillator of the type in which the present invention may be embodied, employing a transvenous/subcutaneous electrode system.

FIG. 1 illustrates an implantable pacemaker/cardioverter/defibrillator 100 and its associated lead system, as implanted in and adjacent to the heart. As illustrated, the lead system comprises a coronary sinus lead 110, a right ventricular lead 120, and a subcutaneous lead 130. The coronary sinus lead is provided with an elongated electrode located in the coronary sinus and great vein region 112, extending around the heart until approximately the point at which the great vein turns downward, toward the apex of the heart. The right ventricular lead 120, corresponds to the lead illustrated in FIG. 1, and includes an elongated defibrillation electrode 122, a ring electrode 124, and helical electrode 126, which is screwed into the tissue of the right ventricle at the right ventricular apex. Leads 110 and 120 may correspond to the leads disclosed in allowed U.S. Pat. Ser. No. 07/284,955 by Bardy for an "Endocardial Defibrillation Electrode System", filed Dec. 15, 1988 and incorporated herein by reference in its entirety. A subcutaneous lead 130 is also illustrated, generally implanted subcutaneously in the left chest. Lead 130 includes a large surface electrode pad 132, carrying elongated electrode coils 136, 138 and 140. Electrode 132 may correspond to the electrode illustrated in allowed U.S. patent application Ser. No. 07/376,730, by Lindemans et al. for a Medical Electrical Lead, filed Jul. 7, 1989 and incorporated herein by reference in its entirety.

Figure 2:
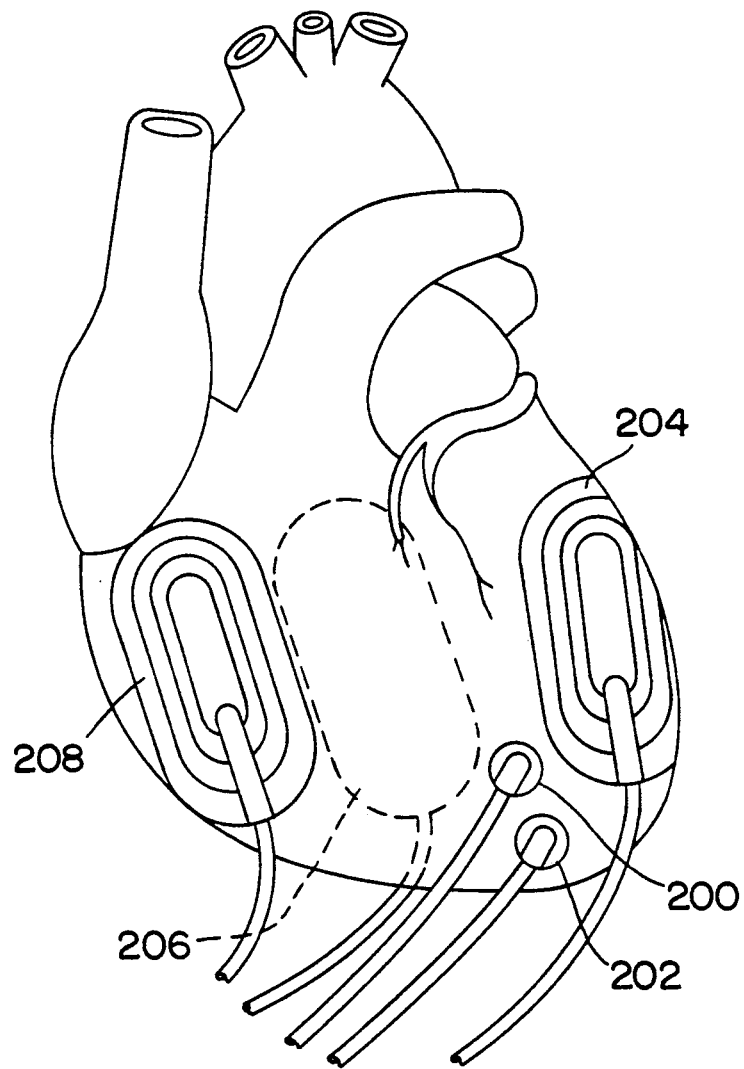
FIG. 2 illustrates a myocardial/epicardial electrode system appropriate for use with a pacemaker/cardioverter/defibrillator embodying the present invention.

FIG. 2 illustrates an epicardial and myocardial electrode system for use in conjunction with an implantable pacemaker/cardioverter/defibrillator. In this case, two unipolar myocardial electrodes 200 and 202 are located on the left ventricle of the heart. These electrodes may correspond to those illustrated in U.S. Pat. No. 3,737,579, issued to Bolduc, on Jun. 5, 1973, and incorporated herein by reference in its entirety. Also illustrated are three large surface electrodes 204, 206 and 208, spaced around the ventricles of the heart. These electrodes may correspond to the electrodes disclosed in U.S. Pat. No. 4,817,634, issued to Holleman et al. on Apr. 4, 1989, also incorporated herein by reference in its entirety.

FIG. 3d is a functional schematic diagram of an implantable pacemaker/cardioverter/defibrillator in which the present invention may usefully be practiced. This diagram should be taken as exemplary of the type of device in which the invention may be embodied, and not as limiting, as it is believed that the invention may usefully be practiced in a wide variety of device implementations, including devices having functional organization similar to any of the implantable pacemaker/defibrillator/cardioverters presently being implanted for clinical evaluation in the United States. The invention is also believed practicable in conjunction with implantable pacemaker/cardioverters/ defibrillators as disclosed in prior U.S. Pat. No. 4,548,209, issued to Wielders et al. on Oct. 22, 1985, U.S. Pat. No. 4,693,253, issued to Adams et al. on Sep. 15, 1987, U.S. Pat. No. 4,830,006, issued to Haluska et al. on May 6, 1989, and U.S. Pat. No. 4,949,719, issued to Pless on Aug. 21, 1990, all of which are incorporated herein by reference in their entireties.

The device is illustrated as being provided with six electrodes, 500, 502, 504, 506, 508 and 510. Electrodes 500 and 502 may be, for example, a pair of electrodes located in the ventricle, for example, corresponding to electrodes 124 and 126 in FIG. 1. Electrode 504 may correspond to a remote, indifferent electrode located on the housing of the implantable pacemaker/cardioverter/defibrillator.

Electrodes 506, 508 and 510 may correspond to the large surface area electrodes located on the ventricular, coronary sinus and subcutaneous leads illustrated in FIG. 1 or to the epicardial electrodes 204,206 and 208 of FIG. 2.

Electrodes 500 and 502 are coupled to the R-wave detector circuit, comprising bandpass filter circuit 514, an automatic gain control circuit 516 for providing an adjustable sensing threshold as a function of the measured R-wave amplitude and a comparator 518. A signal is generated on R-out line 564 whenever the signal sense between electrodes 500 and 502 exceeds the present sensing threshold defined by the automatic threshold adjustment circuit 516. As illustrated, the gain on the band pass amplifier 514 is also adjustable by means of a signal from the pacer timing and control circuitry 520 on GAIN ADJ line 566.

The operation of this R-wave detection circuitry may correspond to that disclosed in commonly assigned, copending U.S patent application Ser. No. 07/612,760 by Keimel, et al., filed Nov. 15, 1990, for an "Apparatus for Electrical Physiologic Signals, incorporated herein by reference in its entirety. However, alternative R-wave detection circuitry such as that illustrated in U.S. Pat. No. 4,819,643, issued to Menken et al. On Apr. 11, 1989 or U.S. Pat. No. 4,800,004, issued to Baker on Nov. 14, 1989, all incorporated herein by reference in their entireties, may also usefully be employed to practice the present invention.

For purposes of the present application, it should be understood that the threshold adjustment circuit 516 sets a threshold corresponding to a predetermined percentage of the amplitude of a sensed R-wave, which threshold decays to a minimum threshold level over a period of less than three seconds thereafter, similar to the automatic sensing threshold circuitry illustrated in the article "Reliable R-wave Detection from Ambulatory Subjects", by Thakor et al. published in Biomedical Science Instrumentation, Vol. 6, pp 67-72, 1978, incorporated herein by reference in its entirety. However, in the context of the present invention, it is preferable that the threshold level not be adjusted in response to paced R-waves, but instead should continue to approach the minimum threshold level following paced R-waves to enhance sensing of low level spontaneous R-waves associated with tachyarrhythmias. The invention may also be practiced in conjunction with more traditional R-wave sensors of the type comprising a band pass amplifier and a comparator circuit to determine when the bandpassed signal exceeds a predetermined, fixed sensing threshold.

Switch matrix 512 is used to select which of the available electrodes are coupled to amplifier 534. Selection of which two electrodes are employed is controlled by the microprocessor 524 via data/address bus 540. Signals from the selected electrodes are passed through bandpass amplifier 534 and into multiplexor 532, where they are converted to multibit digital signals by A/D converter 530, for storage in random access memory 526 under control of direct memory access circuit 528. Microprocessor 524 may analyze the digitized ECG signal stored in random access memory 526 to identify waveform characteristics, if desired.

The remainder of the circuitry is dedicated to the provision of cardiac pacing, cardioversion and defibrillation therapies. The pacer timing/control circuitry 520 includes programmable digital counters or timers which control the basic time intervals associated with VVI mode cardiac pacing, including the pacing escape intervals, the refractory periods during which sensed R-waves are ineffective to restart timing of the escape intervals and the pulse width of the pacing pulses. The durations of these intervals are determined by microprocessor 526, and are communicated to the pacing circuitry 520 via address/data bus 540. The counters and timers within pacing control circuitry 520 are also used to control the timing and duration of cardioversion and defibrillation pulses under control of microprocessor 524. Pacer timing/control circuitry 520 also determines the amplitude of the cardiac pacing pulses and the gain of bandpass amplifier, under control of microprocessor 524.

During VVI mode pacing, the escape interval counter within pacer timing/control circuitry 520 is reset upon sensing of an R-wave as indicated by a signal on line 564, and its timeout triggers generation of a pacing pulse by pacer output circuitry 522, which is coupled to electrodes 500 and 502. The escape interval counter is also reset on generation of a pacing pulse, and thereby controls the basic timing of cardiac pacing functions, including anti-tachy pacing. The duration of the interval defined by the escape interval timer is determined by microprocessor 524, via data/address bus 540. The value of the count present in the escape interval counter when reset by sensed R-waves may be used to measure the duration of R-R intervals, to detect the presence of tachycardia and to determine whether the minimum rate criteria are met for detection of tachycardia or fibrillation.

Microprocessor 524 operates as an interrupt driven device, and is awakened by interrupts from pacer timing/control circuitry 520 corresponding to the occurrence of sensed R-waves and corresponding to the generation of cardiac pacing pulses. These interrupts are provided via data/address bus 540. Any necessary mathematical calculations to be performed by microprocessor 524 and any updating of the values or intervals controlled by pacer timing/control circuitry 520 take place following such interrupts.

In the event that a tachyarrhythmia is detected, and an antitachyarrhythmia pacing regimen is desired, appropriate timing intervals for controlling generation of antitachy pacing therapies are loaded from microprocessor 524 into the pacer timing and control circuitry 520, to control the operation of the escape interval counter and to define refractory periods during which detection of an R-wave by the R-wave detection circuitry is ineffective to restart the escape interval counter. Similarly, in the event that generation of a cardioversion or defibrillation pulses required, microprocessor 524 employs the escape interval counter in pacer timing and control circuitry 520 to control timing of such cardioversion and defibrillation pulses, as well as associated refractory periods during which sensed R-waves are ineffective to reset the timing circuitry.

In response to the detection of fibrillation or a tachycardia requiring delivery of a cardioversion pulse, microprocessor 524 activates cardioversion/defibrillation control circuitry 554 which initiates charging of the high voltage capacitors 556, 558, 560 and 562 via charging circuit 550, under control of high voltage charging line 552. The voltage on the high voltage capacitors is monitored via VCAP line 538, which is passed through multiplexer 532, and, in response to reaching a predetermined value set by microprocessor 524, results in generation of a logic signal on CAP FULL line 542, terminating charging. Thereafter, timing of the delivery of the defibrillation or cardioversion pulse is controlled by pacer timing/control circuitry 520 under control of microprocessor 524. One embodiment of an appropriate system for delivery and synchronization of cardioversion and defibrillation pulses, and controlling the timing functions related to them is disclosed in more detail in copending, commonly assigned U.S. patent application Ser. No. 07/612,761, by Keimel, for an "Apparatus for Detecting and Treating a Tachyarrhythmia", filed Nov. 15, 1990, incorporated herein by reference in its entirety. However, any known cardioversion or defibrillation pulse generation circuitry which allows selection among the available large surface cardioversion or defibrillation electrodes is believed usable in conjunction with the present invention. For example, circuitry controlling the generation of cardioversion and defibrillation pulses as disclosed in U.S. Pat. No. 4,384,585, issued to Zipes on May 24, 1983, U.S. Pat. No. 4,949,719, issued to Pless et al. on Aug. 21, 1990, and U.S. Pat. No. 4,357,817, issued to Engle et al. on Mar. 8, 1983, all incorporated herein by reference in their entireties may also be employed. Similarly, known circuitry for controlling the generation of antitachycardia pacing pulses as described in U.S. Pat. No. 4,577,633, issued to Berkovits on Mar. 25, 1986, U.S. Pat. No. 4,880,005, issued to Pless et al. on Nov. 14, 1989, U.S. Pat. No. 7,726,380, issued to Vollmann et al. on Feb. 23, 1988 and U.S. Pat. No. 4,587,970, issued to Holley et al. on May 13, 1986, all of which are incorporated herein by reference in their entireties may also be used.

In the present invention, sequential or simultaneous discharging of the first and second capacitor banks (capacitors 556, 558, 560, 562) through one or more pathways defined by electrodes 506, 608, 510 is accomplished by output circuit 548, under control of cardioversion/defibrillation control circuitry 524 via control bus 546. Output circuit 548 determines which of the high voltage electrodes 506, 508 and 510 will be employed in delivering the defibrillation or cardioversion pulse regimen, and may also be used to specify a multielectrode, simultaneous pulse regimen, a multielectrode sequential pulse regimen or a pulse regimen employing only a single pair of electrode. One example of circuitry which may be used to perform this function is set forth in commonly assigned copending U.S. patent application Ser. No. 07/612,758, for an "Apparatus for Delivering Single and Multiple Cardioversion and Defibrillation Pulses", filed by Keimel on Nov. 15, 1990, incorporated herein by reference in its entirety. However, alternative output control circuitry as disclosed in U.S. Pat. No. 4,953,551, issued to Mehra et al. on Sep. 4, 1990 or U.S. Pat. No. 4,800,883 issued to Winstrom et al. on Jan. 31, 1989, both incorporated herein by reference in their entireties, may also be used in the context of the present invention.

Measurement of the impedance of an electrode pathway may be performed using any of a number of impedance measurement techniques known to the art. For example, in the case of an implantable cardioverter/defibrillator which regulates the energy delivered by controlling the voltage to which the output capacitors are charged and by regulating the width of the pulse, impedance can be measured by measuring the voltage differential between the leading and trailing edges of the pulse, as set forth in U.S. Pat. No. 4,776,338, issued to Lekholm et al. on Oct. 11, 1988 and in U.S. Pat. No. 4,140,131, issued to Dutcher on Feb. 20, 1979, both of which are incorporated herein by reference in their entireties. A signal reflecting the voltage on the output capacitors after delivery of the defibrillation pulse is readily available on VCAP line 538, accessible to the microprocessor 524 via the A/D converter 530 and data/address bus 540. Following delivery of the defibrillation pulse, the microprocessor may compare the amplitude to which the output capacitors were initially charged, typically controlled by the programming of the device, to the voltage remaining after termination of delivery of the pulse, and calculate the impedance of the pathway over which the pulse was delivered.

Alternatively, the invention may be practiced in cardioverters and defibrillators which regulate the energy delivered by the defibrillation pulse by means of a pulse tilt control, which terminates delivery of the pulse when the voltage on the output capacitor either reaches a predetermined threshold or reaches a predetermined percentage of the initial charging voltage. Such systems are disclosed in U.S. Pat. No. 4,850,357, issued to Bach on Jul. 25, 1989 and in the above-cited U.S. Pat. No. 4,800,883, issued to Winstrom, both of which are incorporated herein by reference in their entireties. In such a system, the microprocessor 524 may either employ the counter within the pacer timing/control circuitry employed to regulate pacing pulse width and check the count on defibrillation pulse termination or may note the actual times of occurrence of pulse initiation and pulse termination, and may use the measured pulse width in conjunction with the known capacitance of the output capacitors and the known initial charging voltage to calculate the impedance of the pathway over which the pulse was delivered.

As noted above, pacer timing and control circuitry 520 includes a plurality of counters which time out intervals associated with the bradycardia pacing. These intervals include a bradycardia pacing escape interval, representing the interval between successive cardiac pacing pulses and between sensed R-waves and the next subsequent cardiac pacing pulses. At the expiration of the brady pacing escape interval, a ventricular pacing pulse is delivered between electrodes 500 and 502. In response to sensing of an R-wave, timing of the escape interval is re-initiated. Pacer circuitry 520 also defines a blanking period, during which R-waves are not sensed by the R-wave amplifier 514 and a refractory period, during which R-waves are sensed, but are ineffective to re-initiate timing of the brady pacing escape interval. Signals indicative of the occurrence of sensed R-waves and cardiac pacing pulses are passed to microprocessor 524 as interrupts, awakening the microprocessor and allowing it to perform any necessary calculations. Microprocessor 524 specifies the values timed by the timers in pacer circuitry 520 by means of control/data bus 540.

R-waves sensed by amplifier 514 are employed by microprocessor 524 in performing tachycardia and fibrillation detection. Tachycardia and fibrillation detection algorithms believed appropriate for use in conjunction with the present invention are disclosed in the article "Onset and Stability for Ventricular Tachyarrhythmia Detection in an Implantable Pacer-Cardioverter-Defibrillator", by Olson et al., published in Computers in Cardiology, Oct. 7-10, 1986, Pages 167-172, IEEE Computer Society Press and incorporated herein by reference in its entirety. However, the present invention is also believed workable in conjunction with any of the numerous alternative fibrillation and tachycardia detection algorithms known to the art, including those disclosed in the above-cited U.S. Pat. No. 4,726,380 issued to Vollmann, U.S. Pat. No. 4,880,005 issued to Pless et al., U.S. Pat. No. 4,830,006 issued to Haluska et al., and U.S. Pat. No. 4,523,595 issued to Zipes. Moreover, it is within the scope of the invention to use physiologic sensors to accomplish detection and characterization of tachyarrhythmias to trigger delivery of cardioversion or defibrillation pulses.

Microprocessor 524 also responds to interrupts indicating the occurrence of sensed R-waves to determine whether previously sensed fibrillation or tachycardias which led to the delivery of cardioversion or defibrillation pulses have terminated. In the context of the present invention, termination of tachycardia can be verified by the sensing of a sequence R-R intervals (intervals separating R-waves), each of which exceeds a predetermined duration indicative of sinus rhythm. Detection of fibrillation termination may be similarly accomplished. Alternatively, any other method of detection of termination of the detected tachyarrhythmia may be employed, including the use of physiologic sensors to detect a return to normal hemodynamic functioning.

Figure 3B:
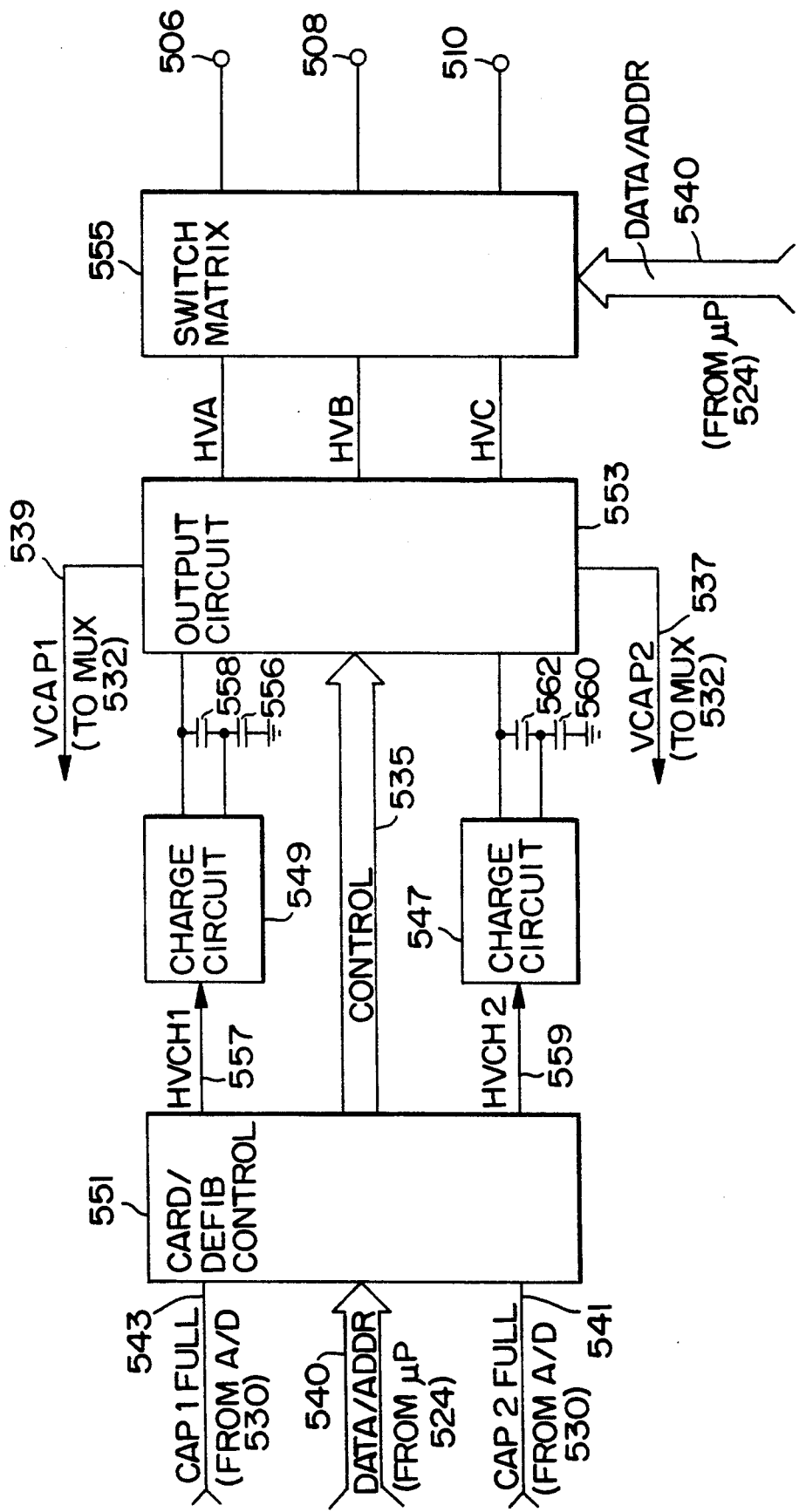

FIG. 3b illustrates the high voltage cardioversion/defibrillation pulse generation pulse generation circuitry and associated control circuitry of an alternative embodiment of the device illustrated in FIG. 3a. The alternative embodiment illustrated is functionally similar to that illustrated in FIG. 3a, with one major difference. In the device as illustrated in FIG. 3b, the two capacitor banks are provided with independently controllable charging circuits, allowing for them to be charged to different voltages. As discussed above, it is believed desirable to be able to regulate the voltage of defibrillation pulses applied across a defibrillation pathway as a function of the measured impedance of the pathway. In order to accomplish this, it is desirable to be able to specify independently controllable charging amplitudes for the capacitor banks couples to the individual pathways. In the context of the embodiment of FIG. 3b, it is to be understood that the microprocessor 524 (FIG. 3a) specifies voltages for each charging circuit independently, and as a function of the measured impedance of the defibrillation pulse pathways. In the device as illustrated, the cardioversion/defibrillation control circuitry 551 corresponds to the cardioversion/defibrillation control circuit 554 (FIG. 3a), with the exception that it is provided with two outputs corresponding to HVCH line 552 in FIG. 3a. These are designated as HVCH 1 line 557 and HVCH 2 line 559. Signals on these lines activate charging circuits 549 and 547, respectively, each of which corresponds to charging circuit 550 as illustrated in FIG. 3a. The voltage on the first capacitor bank (556 and 558) is provided on VCAP 1 line 539. The voltage from the second capacitor bank (560 and 562) is provided on VCAP 2 line 537. Like VCAP line 538 FIG. 3a, these lines provide inputs to the multiplexor 532 (FIG. 3a) whereby they may be provide inputs to the multiplexor 532 (FIG. 3a) whereby they may be provided to the microprocessor 534 via A/D converter 530 (FIG. 3a).

Cardioversion/defibrillation control circuitry 551 also have two inputs corresponding to CAPFULL line 542 in FIG. 3a. These are designated CAPIFULL line 543 and CAP2FULL line 541. These lines contain signals corresponding to that on CAPFULL line 542, and are provided by A/D converter 530, as discussed above in conjunction with FIG. 3a. These signals indicate that the first capacitor bank (556, 558) and the second capacitor bank (560, 562), respectively have reached the voltage specified by the microprocessor, and function to turn off the charging signals on HVCH 1 line 557 and HVCH 2 line 559, respectively. Also provided as an input to cardioversion/defibrillation control circuitry 551 is the data/address bus 540 from the microprocessor 524 (FIG. 3a). By means of signals applied on this bus, the microprocessor controls the pulse regimen (e.g., sequential, simultaneous, single) to be provided by the output circuit. This information is passed through the control circuit 551 to the output circuit 553 via control bus 535, which corresponds to control bus 546 in FIG. 3a. As in the case of the output circuit 548 illustrated in FIG. 3a, output circuit 553 may couple one of the capacitive banks across output lines HVA and HVC, and the other of the capacitor banks across output lines HVB and HVC. However, because the charging circuits 547 and 549 are independent from one another, the voltage is applied across lines HVA-HVC and HVB-HVC may differ from one another, as a function of the impedance of the defibrillation pathway defined by the electrodes to which output lines HVA, HVB and HVC are coupled.

Also illustrated is an optional switch matrix 555, controlled by microprocessor 524, (FIG. 3a) via data/address bus 540. Switch matrix 555 is an optional feature which allows selection of which of the electrodes 506, 508 or 510 are coupled to output lines HVA, HVB and HVC. In an embodiment as illustrated in FIG. 3b, it is expected that the switch matrix 555 may be employed to reconfigure the electrode delivery system, and that the stored information as to the electrode pathways to be used will be defined in terms of the electrodes to be employed, with the output lines HVA, HVB and HVC from output circuit 553 coupled accordingly.

The embodiment illustrated in FIG. 3b is believed to be workable in conjunction with either a sequential or a simultaneous pulse regimen, and, as discussed below in conjunction with the description of FIG. 4b, should provide for an increase in the uniformity of current density, as well as an increase in the overall flexibility of the system. It is also believed desirable to regulate the voltage applied as a function of measured impedance in the context of a therapy regimen which employs only a single electrode pair. The embodiment of FIG. 3b is of course capable of providing this feature as well.

Figure 4A:
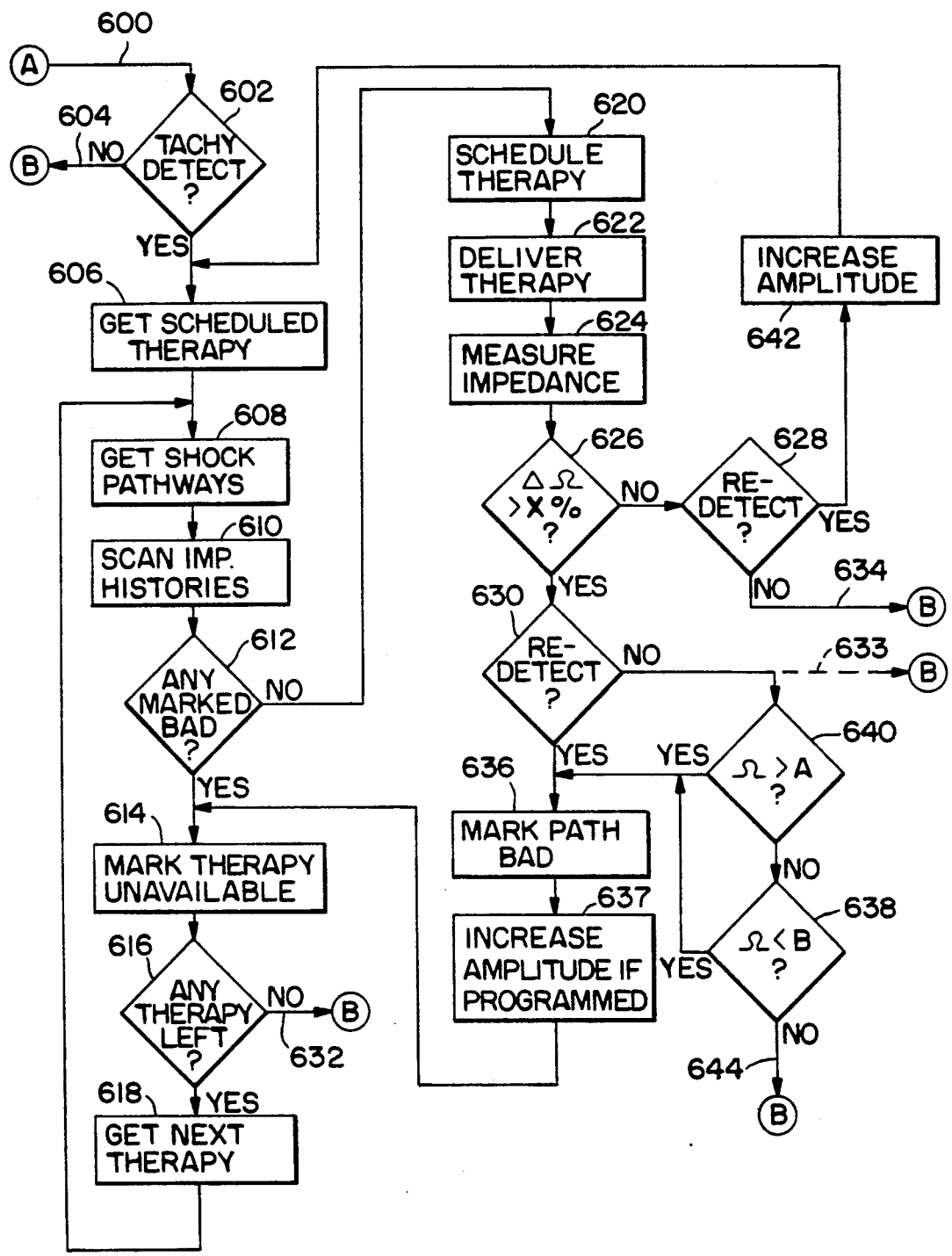
FIGS. 4a, 4b and 4c are functional flow charts illustrating the method of operation of the present invention, as embodied in microprocessor based devices as illustrated in FIGS. 3a and 3b.
Figure 4B:
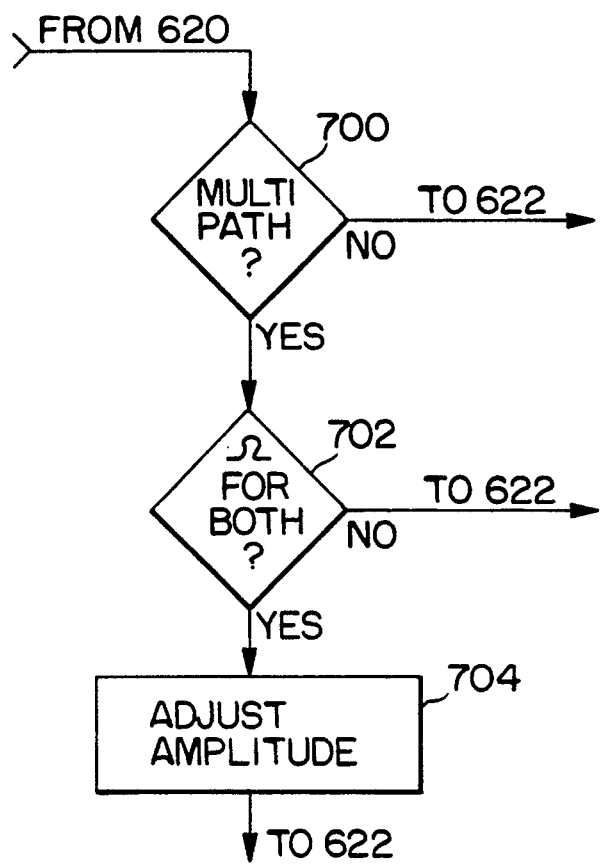
Figure 4C:
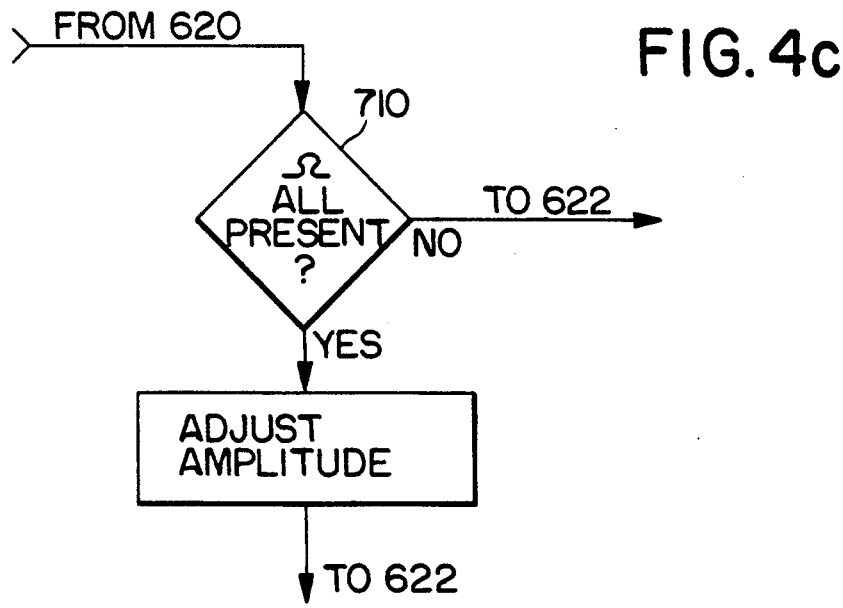

Basic operation of the invention can be understood by reference to the flow chart illustrated in FIGS. 4a, 4b and 4c. These flow charts are intended to reflect the overall function of the device, rather than any particular software or firmware which must be employed in the device. Because the invention is not dependent upon any particular software or hardware configuration in order to be usefully practiced, the flow charts focus on the important functional aspects of the invention and its interrelation to an implantable pacemaker/cardioverter/defibrillator which includes fibrillation and tachycardia detection functions and hardware for initiation of pacing, cardioversion and defibrillation pulses typical of those in products currently in clinical investigation in the United States.

The flow chart of FIG. 4a is entered in response to an interrupt to the microprocessor 524 indicative of a sensed R-wave or the delivery of a pacing pulse which awakens the microprocessor from its sleep state at 600. One of the functions performed in response to such an interrupt is the determination at 602 of whether a tachyarrhythmia is present in the form of either fibrillation or a tachycardia requiring delivery of a cardioversion pulse. In the absence of such detection, the microprocessor goes on to update control functions and time intervals associated with bradycardia or anti-tachycardia pacing at 604, as may be appropriate. In the presence of a tachyarrhythmia requiring delivery of a cardioversion or defibrillation pulse, the random access memory 526 is checked at 606 to determine the currently scheduled electrode configuration and defibrillation pulse regimen. On initial implant or following reprogramming of the device, the scheduled therapy will be the first therapy on the therapy menu. For example, as illustrated in FIG. 5a, the device could be programmed to initially deliver a simultaneous pulse defibrillation regimen, with a second simultaneous pulse defibrillation regimen and single pulse regimens as fallback therapies. Alternatively, the device may be initially programmed to provide a sequential pulse therapy as illustrated in FIG. 5b, with a second sequential pulse regimen and single pulse regimens as backups.

The microprocessor 524 determines the pulse pathways associated with the scheduled therapies at 608 and scans the appropriate impedance histories stored in random access memory 526, as indicated at 61?. If the currently scheduled therapy includes a pathway marked "bad", as indicated at 612, the currently scheduled therapy is canceled, and the therapy is either deleted from the therapy menu, or otherwise designated as unavailable at 614. In the therapy menus illustrated in FIGS. 5a and 5b, both of the first listed therapies are designated as unavailable.

The microprocessor 524 next checks to see whether any available therapies remain on the therapy menu at 616. If not, the microprocessor returns to the portions of its software dedicated to control of bradycardia and tachycardia pacing functions at 532. If an available therapy is found, it is retrieved at 618 and it too is checked to determine whether the pathways associated with the therapy have been marked "bad" at 608. Assuming that no pathways employed in the new therapy have been marked as "bad", the therapy is designated as the currently scheduled therapy regimen at 620 and is delivered at 622. Measurement of the impedance along the pathways employed in delivering the therapy is taken at 624. This measured impedance is stored in an impedance history log of the type illustrated in FIGS. 6a and 6b, along with the time of therapy delivery as indicated in FIGS. 6a and 6b. At this point, the microprocessor awaits subsequent ventricular sensing interrupts and ventricular pacing interrupts in order to allow it to determine whether the delivered therapy was successful in terminating the tachyarrhythmia. As discussed above, a typical mechanism for detection of termination is the presence of a predetermined number of sequential measured R-R intervals in excess of either the detection criteria indicative of the occurrence of the tachyarrhythmia, or a series of R-R intervals otherwise indicative of a return to normal sinus rhythm. Alternatively, termination may be detected using a hemodynamic sensor, such as a pressure sensor, which may be used to identify a return to a normal cardiac output. If the measured impedances did not deviate more than the desired predetermined percentage at 626 from the previously measured impedances, and the therapy was ineffective to terminate the tachyarrhythmia at 628, the therapy will typically be reapplied with the energy level incremented until the maximum available energy level has been reached, as indicated at 642.

In the event that the measured impedance change did exceed the predetermined percentage at 626, and the tachyarrhythmia was redetected at 630, the microprocessor marks the pathway displaying the excessive impedance change as "bad" at 636. Optionally, the pulse amplitude for the next therapy is incremented at 637. The previously delivered therapy is then marked unavailable at 614.

In the event that tachyarrhythmia is not redetected following delivery of the therapy, regardless of whether the detected change in impedance exceeded the predetermined percentage, the therapy delivered may remain scheduled as the current therapy and remains available on the therapy menu. The microprocessor, in this case, may return to that portion of its programming devoted to tachycardia and bradycardia pacing. However the measured impedances may optionally also be computed to predetermined impedances "A" and "B", as illustrated at 638 and 640. These impedances are either fixed impedances which are felt to conclusively indicate a short circuit or an open circuit or impedances reflecting a percentage change substantially in excess of the impedance change threshold at 626. In response to such a detected extreme impedance, the microprocessor may optionally label the pathway involved as bad at 636 and indicate the therapy involved to be unavailable at 614 regardless of the success of the therapy in terminating the arrhythmia.

In FIG. 4a, at 626, 638 and 640, the measured impedances are compared to previously measured impedances in order to determine whether a substantial change has occurred. These previously measured impedances may be impedances as initially measured in the first time the pathway is used, for example impedance measurements taken during initial testing associated with the implant of the device. Alternatively the prior impedance measurements may be made after implant and may represent the most recent measurement or the average of the most recent set of measurements. Yet another alternative would be to use programmed reference values set by the physician in place of actual measurements, and compare the current measured impedances to these reference values.

FIGS. 5a and 6a, together, provide an illustrative example of the operation of the present invention. As indicted in 5a, the physician has programmed the therapy menu by specifying two simultaneous pulse regimens and two single pulse regimens. The impedance history in FIG. 6a illustrates the results of applying the therapies on the therapy menu. The first two times that therapy number one is applied, it is successful, and the measured variation in impedance is less than the predetermined percentage of change specified at 626 (FIG. 4). The third time the simultaneous pulse regimen is delivered, the impedance shows a significant change, being reduced from 60 to 15 ohms for the combined impedance across the electrode system and the delivered pulses are unsuccessful in terminating the detected tachyarrhythmia. Rather than retry the therapy at a higher amplitude, the device instead changes its electrode configuration and pulse regimen to correspond with therapy number two, marking therapy number one as unavailable in FIG. 5a and marking the current pathway associated with the therapy as bad in FIG. 6a. After redetection of the tachyarrhythmia, therapy number two is applied, and it is successful in terminating the tachyarrhythmia, allowing the pathway to remain marked "good" in the impedance history, and allowing therapy number two to remain available on the therapy menu.

For example, the therapies referred to in FIG. 5a may correspond to therapies available for delivery using an electrode system having a coronary sinus electrode (HVA), a subcutaneous plate electrode (HVB) and a right ventricular electrode (HVC). In response to the failure to terminate in conjunction with a measured impedance change exceeding the predetermined percentage specified, the device reconfigures its electrode configuration to deliver pulses using the right ventricular and coronary sinus electrodes tied together, and a pulse delivered between these two electrodes and the subcutaneous plate electrode (HED), indicated as therapy two. Because the coronary sinus and right ventricular electrodes are tied together during delivery of this therapy anyway, their close spacing or contact is not problematic in the context of this particular pulse regimen.

FIGS. 5b and 6b may illustrate a corresponding therapy menu and impedance history for device programmed by the physician to initially deliver pulses in a sequential pulse, multi-electrode regimen as set forth at 5b. Again, it may be assumed that a coronary sinus (HVA), a subcutaneous (HVD) and a right ventricular electrode (HVC) are used. Similar to the sequence illustrated in conjunction with FIGS. 5a and 6a, the first two attempts to deliver therapy number one are successful, and the third attempt is unsuccessful, coupled with a measured increase in the impedance along one of the two defibrillation pathways, as illustrated in FIG. 6b. In response to detection that the pulse pathway between the coronary sinus and right ventricular electrode has developed a rapid increase in impedance, in conjunction with a failure to terminate the sensed tachyarrhythmia, the device changes to a second sequential pulse defibrillation therapy number two, in which the HVA-HVC pathway is not used. As indicated in FIG. 6b, the first time this therapy is tried, it is successful, allowing both pathways associated with delivery of the therapy to remain marked as "good".

It should be noted with regard to FIGS. 6a and 6b that the impedance histories are illustrated as retaining only the three most recent impedance measurements along the particular pathway involved. However, a more lengthy measurement of the impedance record may also be provided if desired. Further, while the method discussed above envisions comparing the measured impedance with the immediately preceded impedance, it may in some cases be desirable to compare the measured impedance with an average of two or more previously measured impedances to determine whether the change in impedance should be considered significant.

FIGS. 4b and 4c illustrate optional additional portions of the operative flowchart of FIG. 4a. As illustrated, the flowcharts of FIGS. 4b and 4c would be inserted between blocks 620 and 622 in FIG. 4a. The flowcharts of FIGS. 4b and 4c illustrate the additional processing required in the case of an embodiment as illustrated in FIG. 3b, in which pulse amplitudes are independently selectable for individual defibrillation pathways. For purposes of the discussion of FIG. 4b, it should be assumed that in addition to programming a therapy menu indicating a preferred order of pathways and pulse regimens to be employed, the device also works in the fashion of presently available implantable cardioverters/defibrillators, and provides a specified pulse amplitude for each selected therapy, which pulse amplitude increases in response to the failure of a delivered therapy to accomplished cardioversion or defibrillation. This is reflected at 642 in FIG. 4a.

The initial amplitude for each defibrillation therapy type and the succeeding, increased amplitudes are typically preset by the physician by programming. Alternatively, the device may simply automatically increase the amplitude of predetermined percentage until such time as the maximum available amplitude has been reached. In either case, a defined series of pulse amplitudes is provided, which may be used in conjunction with the circuitry of FIG. 3b in two alternative methods to control the voltage of the defibrillation pulses actually delivered across the pathways employed in the selected therapy regimen.

The first alternative approach is illustrated in FIG. 4b. In FIG. 4b, it is to be assumed that the defined voltage is intended to be the maximum voltage available for application. In this case, the software of FIG. 4b is entered following block 620 in FIG. 4a. The microprocessor checks at 700 to determine whether a multiple path pulse regimen (e.g., simultaneous or sequential) has been selected. If not, a single pulse pathway regimen has been selected, and the microprocessor returns to the flowchart of FIG. 4a at 622, allowing for delivery of the single pathway, single pulse regimen using the predefined voltage. However, if a simultaneous or sequential pulse regimen has been selected, the microprocessor checks at 702 to determine whether impedance measurements have been made for both pathways to be employed. If so, the microprocessor adjusts the pulse amplitude at 704 using the measured impedance values to provide a more uniform current distribution. For example, the programmed pulse amplitude may constitute the maximum available pulse amplitude, which would be applied across the higher impedance pathway, with the voltage applied across the lower impedance pathway equal to the maximum voltage multiplied by the ratio of the lower pathway impedance to the higher pathway impedance. Alternatively, the programmed defined voltage may constitute the minimum voltage, to be applied across the lower impedance pathway, with the voltage to be applied across the higher impedance pathway equal to the programmed voltage multiplied by the impedance for the high impedance pathway divided by the impedance for the low impedance pathway. In either case, a more equal current density should be accomplished.

A second approach is illustrated in FIG. 4c. The flowchart of FIG. 4c presumes that the microprocessor will adjust the voltage of the defibrillation pulse regimen, regardless of whether it is a single or multiple pathway regimen. After selection of a therapy type at 620 (FIG. 4a), the microprocessor may check to see whether the impedance of the pathway or pathways involved in the defibrillation pulse regimen selected have been previously measured. If so, these measured values are used to adjust the output voltage. In this case, the microprocessor may assume that the programmed or physician specified voltage for the therapy is based upon an assumption of a reference impedance value, for example 50 or 100 ohms. The actual impedance across the pathway may be compared to the measured impedance, and the voltage of the defibrillation pulse to be applied across the pathway recalculated to provide a pulse corresponding to a pulse of the programmed amplitude and pulse duration or tilt, applied across the reference impedance value. Thus, if the measured impedance is less than the reference impedance, the microprocessor will specify a lower voltage to be applied across that pathway than the programmed voltage. If the impedance of the pathway is higher than the reference impedance, the microprocessor will specify a higher voltage than programmed. This voltage adjusted system is as applicable to single pulse, single pathway defibrillation pulse therapies as to multi-electrode, multiple path defibrillation pulse therapies.

Turning to the flowchart of FIG. 4c, the flowchart is entered following selection of the therapy type to be delivered at 620, and, if impedance amplitude measurements are found to be present for all pathways at 710, new values for the pulse voltages are calculated at 712. If, on the other hand, there are no pre-existing measurements for the impedance, the programmed pulse amplitudes will be employed and the impedance measurement taken in conjunction with delivery of the therapy at 622 and 624 (FIG. 4a) will be used to allow for adjustment of the defibrillation pulse voltage in subsequent applications of the same therapy or other therapies employing the measured pathways.

The above specification and the embodiments disclosed are intended to allow one of skill in the art to incorporate the present invention into a modern implantable cardioverter/defibrillator. However, it is of course understood that the particular implementation of the invention will vary depending upon the particular underlying circuitry types and software systems employed. As such, the above disclosure should be considered exemplary, rather than limiting with regard to the claims that follow.

In conjunction with the above disclosure, we claim:

1. An implantable cardioverter or defibrillator, comprising:
   means for detecting the presence of a tachyarrhythmia;
   pulse generator means for delivering a cardioversion or defibrillation pulse regimen in response to detection of a tachyarrhythmia by said detection means;
   electrode means for delivering said cardioversion or defibrillation pulse regimen to a heart, said electrode means comprising a plurality of electrodes, said electrodes defining a plurality of pulse pathways between ones of said electrodes;
   means for selecting which of said defibrillation pathways are to be employed during the delivery of said defibrillation or cardioversion pulse regimen;
   means for measuring the impedance of each of said selected pathways during delivery of said cardioversion or defibrillation regimen;
   means for defining a reference impedance for each of said selected pathways;
   means for comparing each said measured impedance associated with delivery of said cardioversion or defibrillation pulse regimen with a said reference impedance for each said selected pathway to determine whether said measured impedance differs by more than a predetermined amount from said reference impedance;
   means for determining whether said cardioversion or defibrillation pulse regimen was effective to terminate said detected tachyarrhythmia; and
   means responsive to said comparing means and to said determining means for rendering any said pathway for which said measured impedance differs by more than said previous predetermined amount from said reference impedance unavailable for future cardioversion or defibrillation regimens, provided that said cardioversion or defibrillation pulse regimen is determined to be ineffective in terminating said detected tachyarrhythmia.

2. An implantable cardioverter or defibrillator according to claim 1 wherein said means for selecting further comprising means for selecting a defibrillation or cardioversion pulse regimen for subsequent use which does not employ said unavailable pathway.

3. An implantable cardioverter or defibrillator according to claim 1 or claim 2 wherein said means for defining a reference impedance comprises memory means for storing said measured impedances and wherein each said reference impedance comprises an impedance measurement stored in said memory means.

4. An implantable cardioverter or defibrillator according to claim 1 or claim 2 further comprising means for incrementing the amplitude of a subsequent cardioversion or defibrillation pulse regimen in response to said determining means determining that a previous cardioversion or defibrillation pulse regimen was ineffective to terminate said detected tachyarrhythmia.

5. An implantable cardioverter or defibrillator according to claim 1 or claim 2 further comprising means for adjusting the amplitude of a subsequent cardioversion or defibrillation pulse regimen in response to the measurement of the impedances of said selected pathways during delivery of said cardioversion or defibrillation pulse regimen.

6. An implantable cardioverter or defibrillator, comprising:
   means for detecting the presence of a tachyarrhythmia;
   pulse generator means for delivering a cardioversion or defibrillation pulse regimen in response to detection of a tachyarrhythmia by said detection means;
   electrode means for delivering said cardioversion or defibrillation pulse regimen to a heart, said electrode means comprising a plurality of electrodes, said electrodes defining a plurality of pulse pathways between ones of said electrodes;
   means for defining a first cardioversion or defibrillation pulse regimen and for selecting a set of said electrodes and a set of said defibrillation pathways to be employed during the delivery of a said first cardioversion or defibrillation pulse regimen;
   means for defining a reference impedance for each of said selected pathways;
   means for measuring the impedance of each of said selected pathways during delivery of said first cardioversion or defibrillation pulse regimen;
   means for comparing each said measured impedance associated with delivery of said first cardioversion or defibrillation pulse regimen with a reference impedance for each said selected pathway to determine whether said measured impedance differs by more than a predetermined amount from said reference impedance; and wherein
   said selecting means is responsive to aid comparing means to define a second cardioversion or defibrillation pulse regimen employing all of said set of electrodes selected to deliver said first cardioversion or defibrillation regimen and which does not employ any said selected pathway for which said measured impedance differs by more than said predetermined amount from said reference impedance.

7. An implantable cardioverter or defibrillator according to claim 6 wherein said selecting means further comprises;
   means for determining whether said cardioversion or defibrillation pulse regimen was effective to terminate said detected tachyarrhythmia; and
   means responsive to said comparing means and to said determining means for rendering any said selected pathway for which said measured impedance differs by more than said predetermined amount from said reference impedance unavailable for delivery of future cardioversion or defibrillation regimens when that said cardioversion or defibrillation pulse regimen is determined to be ineffective to terminate said detected tachyarrhythmia.

8. An implanted cardioverter or defibrillator according to claim 6 or claim 7 wherein said means for defining a reference impedance comprises memory means for storing said measured impedances and wherein each said reference impedance comprises an impedance measurement stored in said memory means.

9. An implantable cardioverter or defibrillator according to claim 7 further comprising means for incrementing the amplitude of a subsequent cardioversion or defibrillation pulse regimen in response to said determining means determining that a previous cardioversion or defibrillation pulse regimen was ineffective to terminate said detected tachyarrhythmia.

10. An implantable cardioverter or defibrillator according to claim 6 or claim 7 further comprising means for adjusting the amplitude of a subsequent cardioversion or defibrillation pulse regimen in response to the measurement of the impedances of said selected pathways during delivery of said cardioversion or defibrillation pulse regimen.

* * * * *